United States Patent
Cherpes et al.

(10) Patent No.: US 10,835,601 B2
(45) Date of Patent: *Nov. 17, 2020

(54) METHODS AND COMPOSITIONS RELATED TO ACCELERATED HUMORAL AFFINITY

(71) Applicant: OHIO STATE INNOVATION FOUNDATION, Columbus, OH (US)

(72) Inventors: Thomas Cherpes, Columbus, OH (US); Nirk E. Quispe Calla, Hilliard, OH (US); Rodolfo Daniel Vicetti Miguel, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/775,155

(22) PCT Filed: Nov. 9, 2016

(86) PCT No.: PCT/US2016/061062
§ 371 (c)(1),
(2) Date: May 10, 2018

(87) PCT Pub. No.: WO2017/083337
PCT Pub. Date: May 18, 2017

(65) Prior Publication Data
US 2018/0369366 A1    Dec. 27, 2018

Related U.S. Application Data

(60) Provisional application No. 62/253,370, filed on Nov. 10, 2015.

(51) Int. Cl.
| | | |
|---|---|---|
| *A61K 39/39* | (2006.01) | |
| *A61K 39/118* | (2006.01) | |
| *A61K 39/05* | (2006.01) | |
| *A61K 39/21* | (2006.01) | |
| *C12N 7/00* | (2006.01) | |
| *A61K 39/00* | (2006.01) | |

(52) U.S. Cl.
CPC ............. *A61K 39/39* (2013.01); *A61K 39/05* (2013.01); *A61K 39/118* (2013.01); *A61K 39/21* (2013.01); *C12N 7/00* (2013.01); *A61K 2039/521* (2013.01); *A61K 2039/545* (2013.01); *A61K 2039/55594* (2013.01); *A61K 2039/575* (2013.01); *A61K 2039/70* (2013.01); *C12N 2740/16134* (2013.01); *C12N 2740/16171* (2013.01)

(58) Field of Classification Search
None
See application file for complete search history.

(56) References Cited

U.S. PATENT DOCUMENTS

| | | | |
|---|---|---|---|
| 5,759,551 A | 6/1998 | Ladd et al. | |
| 5,843,446 A | 12/1998 | Ladd et al. | |
| 6,001,372 A | 12/1999 | Demars et al. | |
| 6,465,251 B1 | 10/2002 | Schultze et al. | |
| 6,653,461 B2 | 11/2003 | Demars et al. | |
| 7,851,609 B2 | 12/2010 | Jackson | |
| 7,964,200 B2 | 6/2011 | Mrsny et al. | |
| 8,309,102 B2 | 11/2012 | Mrsny et al. | |
| 8,318,906 B2 | 11/2012 | Braun et al. | |
| 8,757,792 B2 | 6/2014 | Takano | |
| 2001/0026932 A1 | 10/2001 | Thomas et al. | |
| 2002/0072093 A1 | 6/2002 | Chen et al. | |
| 2002/0142001 A1 | 10/2002 | Brunham | |
| 2003/0118569 A1 | 6/2003 | Bankert | |
| 2004/0126389 A1 | 7/2004 | Berthet et al. | |
| 2006/0121055 A1* | 6/2006 | Campbell | A61K 31/716 424/209.1 |
| 2006/0166344 A1* | 7/2006 | Pizza | A61K 39/095 435/183 |
| 2006/0234260 A1 | 10/2006 | Griffais et al. | |
| 2006/0240038 A1* | 10/2006 | Fensterle | A61K 35/13 424/204.1 |
| 2008/0113933 A1 | 5/2008 | Murdin et al. | |
| 2008/0305112 A1 | 12/2008 | Grandi et al. | |
| 2009/0022755 A1 | 1/2009 | Barth et al. | |
| 2010/0297164 A1* | 11/2010 | Grandi | A61K 39/118 424/192.1 |
| 2013/0345277 A1 | 12/2013 | Wandinger-Ness et al. | |

(Continued)

FOREIGN PATENT DOCUMENTS

| | | |
|---|---|---|
| CN | 100490895 C | 5/2009 |
| DE | 19954514 | 5/2001 |

(Continued)

OTHER PUBLICATIONS

Wolf et al. Infection and Immunity, May 2001, vol. 69, No. 5 p. 3082-p. 3091.*
Definition of kit. https://www.lexico.com/en/definition/kit retrieved Sep. 23, 2019.*
Formulation: www.cambridgemedchemconsulting.com/resources/formulation.html retrieved on Mar. 19, 2020.*
International Searching Authority, U.S. International Search Report and Written Opinion. PCT Application PCT/US2016/061062, dated Jan. 23, 2017. 19 pages.

(Continued)

*Primary Examiner* — Oluwatosin A Ogunbiyi
(74) *Attorney, Agent, or Firm* — Meunier Carlin & Curfman LLC (57) ABSTRACT

Disclosed herein is a vaccine comprising an antigen and a protein, peptide, or carbohydrate of *Chlamydia* spp., or a fragment thereof, wherein the antigen is not derived from a *Chlamydia* spp. Also disclosed are methods of treating or preventing diseases comprising administering to a subject a vaccine, wherein the vaccine comprises an antigen and a protein, peptide, or carbohydrate of *Chlamydia* spp., or a fragment thereof, wherein the antigen is not derived from a *Chlamydia* spp.

16 Claims, 3 Drawing Sheets (56) References Cited

U.S. PATENT DOCUMENTS

| | | |
|---|---|---|
| 2014/0056967 A1 | 2/2014 | Barth et al. |
| 2014/0275478 A1 | 9/2014 | Follmann et al. |

FOREIGN PATENT DOCUMENTS

| | | | | |
|---|---|---|---|---|
| WO | 1995/012411 A1 | 5/1995 | | |
| WO | 1997/026910 A2 | 7/1997 | | |
| WO | 1998028005 A1 | 7/1998 | | |
| WO | 1999015157 | 4/1999 | | |
| WO | 2001034194 | 5/2001 | | |
| WO | WO-0202606 A2 * | 1/2002 | ........... | C07K 14/295 |
| WO | 2002/028998 A2 | 4/2002 | | |
| WO | 2003/059385 A2 | 7/2003 | | |
| WO | 2005/007189 A1 | 1/2005 | | |
| WO | 2006128296 A1 | 12/2006 | | |
| WO | 2007126163 | 11/2007 | | |
| WO | 2010149394 | 12/2010 | | |
| WO | 2013049941 | 4/2013 | | |
| WO | WO-2014153087 A1 * | 9/2014 | ........... | A61K 39/085 |
| WO | 2015016718 | 2/2015 | | |
| WO | 2016/130667 A1 | 8/2016 | | |

OTHER PUBLICATIONS

Cavallo F et al., Vaccination for treatment and prevention of cancer in animal models. Adv Immunol. 2006. 90:175-213. Review.
O'Hagan D T, et al., MF59 is a safe and potent vaccine adjuvant for flu vaccines in humans: what did we learn during its development? Clin Pharmacol Ther. Dec. 2007; 82(6):740-4.
Clapp T, et al., Vaccines with Aluminum-Containing Adjuvants: Optimizing Vaccine Efficacy and Thermal Stability., J Pharm Sci. Feb. 2011; 100(2):388-401.
Hoft D F, et al., A new recombinant bacille Calmette-Guérin vaccine safely induces significantly enhanced tuberculosis-specific immunity in human volunteers., J Infect Dis. Nov. 15, 2008; 198(10):1491-501.
Houston et al., Protein engineering of antibody binding sites: recovery of specific activity in an anti-digoxin single-chain Fv analogue produced in *Escherichia coli*. Proc. Natl. Acad. Sci. USA 1988, 85:5879-5883.
Bird et al., Single-chain antigen-binding proteins., Science 1988, 242:423-426.
International Report on Patentability issued for Application No. PCT/US2016/061062, dated May 24, 2018.
Extended European Search Report. Issued by the European Patent Office in Application No. EP 16864881.4 dated Jun. 27, 2019. 12 pages.
Macmillan, Lucinda, et al. "A recombinant multivalent combination vaccine protects against Chlamydia and genital herpes." FEMS Immunology & Medical Microbiology 49.1 (2007): 46-55.
Bard, et al., "Chlamydia trachomatis stimulates human peripheral blood B lymphocytes to proliferate and secrete polyclonal immunoglobulins in vitro." Infection and immunity 43.1 (1984): 84-92. XP55637029A.
Findlay, Heather E., Heather McClafferty, and Richard H. Ashley. "Surface expression, single-channel analysis and membrane topology of recombinant Chlamydia trachomatis Major Outer Membrane Protein." BMC microbiology 5.1 (2005): 5.
GenBank Accession No. DQ064295. Chlamydia trachomatis strain L2/434 major outer membrane protein (ompA) gene, complete cds. Jan. 26, 2006.

Heinz, Eva, et al. "Comprehensive in silico prediction and analysis of chlamydial outer membrane proteins reflects evolution and life style of the Chlamydiae." BMC genomics 10.1 (2009): 634.
Hua, et al., "Immunogenicity of a chimeric peptide corresponding to T helper and B Cell Epitopes of the Chlamydia trachomatis major outer membrane protein", J of Experim Med 175 (1992), 227-235.
Levitt, D., R. Danen, and J. Bard. "Both species of chlamydia and two biovars of Chlamydia trachomatis stimulate mouse B lymphocytes." The Journal of Immunology 136.11 (1986): 4249-4254.
Luo, Xin M., et al. "Engineering human hematopoietic stem/progenitor cells to produce a broadly neutralizing anti-HIV antibody after in vitro maturation to human B lymphocytes." Blood 113.7 (2009): 1422-1431.
Massari, et al., "Toll-Like Receptor 2-Dependent Activity of Native Major Outer Membrane Protein Proteosomes of Chlamydia trachomatis", Infection and Immunity 81 (2013), 303-310.
Stephens, Richard S., et al. "Sequence analysis of the major outer membrane protein gene from Chlamydia trachomatis serovar L2." Journal of bacteriology 168.3 (1986): 1277-1.
Wortis, et al., "B-Cell activation by crosslinking of surface IgM or litigation of CD40 involves alternative signal pathways and results in different B-Cell phenotypes", Proc. Natl. Acad. Sci. USA 92 (1995), 3348-3352.
Zhu, et al., "Identification of immunodominant linear B-cell epitopes within the major outer membrane protein of Chlamydia trachomatis", Acta Biochim Biophys Sin (2010): 1-8.
European Patent Office. Extended European Search Report. Issued in European Application No. 16749794.0 dated Jun. 11, 2018.
European Patent Office. Communication pursuant to Aritcle 94(3) EPC. Issued in European Application No. 16749794.0, dated Jan. 30, 2019.
European Patent Office. Communication Pursuant to Article 94(3) EPC issued for European Application No. 16749794.0, dated Nov. 6, 2019.
International Preliminary Report on Patentability issued for PCT Application No. PCT/US2018/024007, dated Oct. 3, 2019.
International Search Report and Written Opinion issued for Application No. PCT/US2018/024007, dated Aug. 2, 2019.
International Preliminary Report on Patentability issued in Application No. PCT/US2016/017338, dated Aug. 24, 2017.
International Search Report and Written Opinion issued for Application No. PCT/US2016/017338, dated May 6, 2016.
Office Action issued for Japanese Application No. 2017-541938, dated Dec. 17, 2019.
Non-Final Office Action issued for U.S. Appl. No. 15/550,110, dated Mar. 14, 2019.
Final Office Action issued for U.S. Appl. No. 15/550,110, dated Sep. 18, 2019.
Office Action and Search Report issued by the Chinese Intellectual Property Administration in Application No. CN 201680009419.0 dated May 11, 2020. 36 pages, including English translation.
Office Action issued by the Australian Intellectual Property Office in Application No. AU 2016219379 dated Jun. 23, 2020. 6 pages.
Communication pursuant to Article 94(3) EPC issued by the European Patent Office in Application No. EP 16749794.0 dated Jun. 15, 2020. 5 pages.
Ingvarsson, Sigurdur, et al. "Antigen-specific activation of B cells in vitro after recruitment of T cell help with superantigen." Immunotechnology 1.1 (1995): 29-39.
Toussi, et al., "Immune Adjuvant Effect of Molecularly-defined Toll-Like Receptor Ligands", Vaccines 2, (2014), 323-353.

* cited by examiner

METHODS AND COMPOSITIONS RELATED TO ACCELERATED HUMORAL AFFINITY

CROSS-REFERENCE TO RELATED APPLICATIONS

This application claims benefit of U.S. Provisional Application No. 62/253,370, filed Nov. 10, 2015, incorporated herein by reference in its entirety.

BACKGROUND

A vaccine is capable of starting a humoral immune response that produces antibodies. Vaccines can also activate lymphocytes, such as cytotoxic T cells, through a cellular immune response that help the host resist invasion of a pathogenic organism or prevent occurrence of disease (Cavallo F et al., Vaccination for treatment and prevention of cancer in animal models. *Adv Immunol.* 2006. 90:175-213. Review). Although vaccines have the effect of activating a subject's immune system, in clinical use, it is often found that the vaccine cannot perform the desired effect in some populations whose immune systems are too weak, such as the aged and children, and thus the addition of the proper amount of vaccine adjuvant is needed. Furthermore, addition of a vaccine adjuvant also has the effect of promoting the immune system to more effectively recognize the antigen, which may help decrease the vaccine dosage or vaccine frequency. Therefore, the addition of a vaccine adjuvant not only can decrease the cost of the vaccine, but it can also increase the immune efficiency of the vaccine.

According to the functions of adjuvants, adjuvants can be classified into two groups. Adjuvants belonging to the first group are used for absorbing antigens and assisting antigens to be phagocytized by cells, such as aluminum salts and M59 emulsifying agent, etc. (O'Hagan D T, Wack A, Podda A. *Clin Pharmacol Ther.* 2007 December; 82(6):740-4; 4. Clapp T, Siebert P, Chen D, Jones Braun L. *J Pharm Sci.* 2011 February; 100(2):388-401). Adjuvants belonging to the second group are immune regulatory factors, such as CFA-mycobacteria, etc. (Hoft D F, Blazevic A, Abate G, Hanekom W A, Kaplan G, Soler J H, Weichold F, Geiter L, Sadoff J C, Horwitz M A. *J Infect Dis.* 2008 Nov. 15; 198(10):1491-501). A new vaccine adjuvant that accelerates humoral immunity, including affinity maturation, is useful in the art. SUMMARY Disclosed herein is a vaccine comprising an antigen and a protein, peptide, or carbohydrate of *Chlamydia* spp., or a fragment thereof, wherein the antigen is not derived from a *Chlamydia* spp.

Also disclosed herein are methods of treating or preventing a disease. These methods comprise administering to a subject an antigen, wherein the antigen is not derived from *Chlamydia* spp.; and a protein, peptide, or carbohydrate of *Chlamydia* spp., or a fragment thereof, thereby preventing a disease or infection in the subject.

Further disclosed is are kits comprising an antigen, and a protein, peptide, or carbohydrate of *Chlamydia* spp., or a fragment thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows that *Chlamydia* displays strong adjuvant activity during induction of antigen-specific humoral immunity. Mice were administered OVA alone or OVA+inactivated *C. trachomatis* L2 elementary bodies (EBs) every 2 weeks for a total of 3 doses. Serum was obtained 2 weeks after each dose.

FIG. 2 shows *Chlamydia* greatly increases the affinity of antigen-specific antibodies.

FIG. 3 shows *Chlamydia* significantly increases diphtheria toxin (DT)-specific antibody levels after only one vaccination. Mice were administered DT alone or DT+inactivated *C. trachomatis* L2 EBs 2 weeks later serum was obtained.

FIG. 4 shows DT vaccination with *Chlamydia* adjuvant increases protection from subsequent lethal DT challenge.

DETAILED DESCRIPTION

Definitions

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +/−0.20% or +/−0.10%, more preferably +/−0.5%, even more preferably +/−0.1%, and still more preferably +/−.0.1% from the specified value, as such variations are appropriate to perform the disclosed methods.

The term "antigenic composition" refers to a composition comprising material which stimulates the immune system and elicits an immune response in a host or subject.

The term "elicit an immune response" refers to the stimulation of immune cells in vivo in response to a stimulus, such as an antigen. The immune response consists of both cellular immune response, e.g., T cell and macrophage stimulation, and humoral immune response, e.g., B cell and complement stimulation and antibody production. Immune response may be measured using techniques well-known in the art, including, but not limited to, antibody immunoassays, proliferation assays, and others.

The term "vaccine" as used herein refers to a composition comprising a recombinant virus as described herein, which is useful to establish immunity to the virus in the subject. It is contemplated that the vaccine comprises a pharmaceutically acceptable carrier and/or an adjuvant. It is contemplated that vaccines are prophylactic or therapeutic.

A "prophylactic" treatment is a treatment administered to a subject who does not exhibit signs of a disease or exhibits only early signs for the purpose of decreasing the risk of developing pathology. The vaccines disclosed herein can be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

The term "inactivated" is used herein to describe a microorganism, such as *Chlamydia* spp. (including *C. trachomatis, C. psittaci* and *C. muridarum*), that is also known in the art as a "killed" or "dead" microorganism. An inactivated bacterium is a whole bacterium without infective properties and is produced from a "live" bacterium, regardless of whether the bacterium has been previously attenuated in any manner.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies can be produced from the vaccines described herein, and may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

An "effective amount" as used herein, means an amount which provides a therapeutic or prophylactic benefit.

As used herein, an "immunoassay" refers to any binding assay that uses an antibody capable of binding specifically to a target molecule to detect and quantify the target molecule.

As used herein, an "instructional material" includes a publication, a recording, a diagram, or any other medium of expression which can be used to communicate the usefulness of a compound, composition, method, platform, or system of the invention in the kit for practicing the methods described herein. The instructional material of the kit of the invention can, for example, be affixed to a container which contains the identified compound, composition, platform, or delivery system of the invention or be shipped together with a container which contains the identified compound, composition, method components, platform, or system of the invention. Alternatively, the instructional material can be shipped separately from the container with the intention that the instructional material and the compound be used cooperatively by the recipient.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician or veterinarian.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal or vaginal fluid, cervical secretions, perspiration, semen, transudate, exudate, and synovial fluid.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. The term "tumor-associated antigen" or "TAA" is used herein to refer to a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention.

The term "B cell" refers to a B lymphocyte. B cell precursors reside in the bone marrow where immature B cells are produced. B cell development occurs through several stages, each stage representing a change in the genome content at the antibody loci. In the genomic heavy chain variable region there are three segments, V, D, and J, which recombine randomly, in a process called VDJ rearrangement to produce a unique variable region in the immunoglobulin of each B cell. Similar rearrangements occur for the light chain variable region except that there are only two segments involved, V and J. After complete rearrangement, the B cell reaches the $IgM^+$ immature stage in the bone marrow. These immature B cells present a membrane bound IgM, i.e., BCR, on their surface and migrate to the spleen, where they are called transitional B cells. Some of these cells differentiate into mature B lymphocytes. Mature B cells expressing the BCR on their surface circulate in the blood and lymphatic system, performing the role of immune surveillance. They do not produce soluble antibodies until they become fully activated. Each B cell has a unique receptor protein that will bind to one particular antigen. Once a B cell encounters its antigen and receives an additional signal from a T helper cell, it can further differentiate into a plasma B cell expressing and secreting soluble antibodies or a memory B cell.

The term "B cell" can also refer to any B lymphocyte which presents a fully rearranged, i.e., a mature, B cell receptor (BCR) on its surface. For example, a B cell can be an immature or a mature B cell and is preferably a naïve B cell, i.e., a B cell that has not been exposed to the antigen specifically recognized by the BCR on the surface of said B cell. The B cells can be memory B cells, preferably $IgG^+$ memory B cells. The term "B cells" can also refer to a mixture of B cells. A mixture of B cells can mean that the B cells in the mixture have different antigen-specificities, i.e., produce antibodies or fully rearranged BCRs which recognize a variety of antigens. The antibodies or BCRs of a single B cell are usually identical, also with respect to antigen-specificity.

The term "B cell secreting antibodies" preferably refers to plasma B cells. The term "B cell carrying a BCR on their surface" preferably refers to B cells expressing a BCR, preferably a fully rearranged BCR, at their plasma membrane. In this context, "a BCR" preferably does not mean a single BCR but preferably means a multitude of BCRs having the same antigen-specificity The term "portion" refers to a fraction. A portion preferably means at least 20%, at least 30%, preferably at least 40%, preferably at least 50%, more preferably at least 60%, more preferably at least 70%, even more preferably at least 80%, and most preferably at least 90% of the entire entity. The term "substantial portion" preferably refers to at least 50%, more preferably at least 60%, more preferably at least 70%, even more preferably at least 80%, even more preferably at least 90%, even more preferably at least 95%, and most preferably at least 99% of the entire entity.

The term "clonal expansion" refers to a process wherein a specific entity is multiplied. In the context of the present invention, the term is preferably used in the context of an immunological response in which lymphocytes, preferably B lymphocytes, are stimulated by an antigen, proliferate, and the number of specific lymphocytes recognizing said antigen is amplified. Preferably, clonal expansion leads to differentiation of the lymphocytes, preferably into lymphocytes producing and secreting antibodies. B lymphocytes secreting antibodies are, for example, plasma B cells.

As used herein, the term "enhanced immune response" refers to increasing the ability of a germinal center to generate specific types of antibodies, e.g., high affinity, broadly neutralizing antibodies, and/or generating antibodies at a higher rate.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

The term "antigen" relates to an agent comprising an epitope against which an immune response is to be generated. The term "antigen" includes, in particular, proteins, peptides, polysaccharides, lipids, nucleic acids, especially RNA and DNA, and nucleotides. The term "antigen" also includes derivatized antigens as secondary substance which becomes antigenic—and sensitizing—only through transformation (e.g., intermediately in the molecule, by completion with body protein), and conjugated antigens which, through artificial incorporation of atomic groups (e.g., isocyanates, diazonium salts), display a new constitutive specificity. In a preferred embodiment, the antigen is a tumor antigen, i.e., a constituent of cancer cells which may be derived from the cytoplasm, the cell surface and the cell nucleus, in particular those antigens which are produced, preferably in large quantity, intracellularly or as surface antigens on tumor cells. Examples are carcinoembryonic antigen, al-fetoprotein, isoferritin and fetal sulfoglycoprotein, α2-H-ferroprotein and γ-fetoprotein and various viral tumor antigens. In a further embodiment, the antigen is a viral antigen such as viral ribonucleoproteins or envelope proteins. In particular, the antigen or peptides thereof should be recognizable by a B cell receptor or an immunoglobulin molecule such as an antibody. Preferably, the antigen if recognized by a B cell receptor is able to induce in presence of appropriate co-stimulatory signals, clonal expansion of the B cell expressing the BCR specifically recognizing the antigen and the differentiation of such B cells into antibody secreting B cells. An antigen can present in a repetitive organization, i.e., the antigen comprises more than one, preferably at least 2, at least 3, at least 4, up to 6, 10, 12 or more agents or epitopes against which an immune response is to be generated or against which the antibodies which are to be produced. Such repetitive antigen preferably is capable of binding to more than one antibody of the same specificity. In other words, such repetitive antigen comprises more than one epitope, preferably identical epitope, and thus is capable of "cross-linking" antibodies directed to said epitope. The more than one agents or epitopes may be covalently or non-covalently linked, wherein a covalent linkage may be by any chemical grouping such as by peptide linkages. An antigen can be a fusion molecule comprising a repetition of an antigen peptide or comprising different antigen peptides having a common epitope. In one preferred embodiment, said antigen peptides are linked by peptide linkers.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Vaccines, Methods, and Kits

It has been discovered that concomitant in vivo administration of a cognate antigen and *Chlamydia* drives development of a robust antigen specific humoral immunity and accelerates development of higher affinity antigen-specific antibodies. For example, disclosed herein is the formation of HIV-1-specific neutralizing antibodies.

Chronic *Chlamydia trachomatis* infection is known to induce germinal center-like structures in genital mucosa, but mechanistic explanation for this observation is undefined. However, it was recently found that *Chlamydia* spp. induce polyclonal B cell activation and proliferation in vitro (humans, nonhuman primates, canines, felines, and mice) and in vivo (mice), and promotes production of non-*Chlamydia*-specific polyclonal antibodies.

This phenomenon can be exploited to increase humoral immune responses against cognate antigen by co-administering an antigen and *Chlamydia*. For example, mice were administered ovalbumin (OVA) and inactivated *C. trachomatis* serovar L2 elementary body (EB) every 2 weeks for a month (i.e., a total of 3 treatments). In this study, these mice displayed significantly higher OVA-specific IgM and IgG serum antibody levels compared to mice receiving OVA alone (FIG. 1), and OVA-specific antibody affinity was significantly higher in mice concomitantly treated with OVA and chlamydial EB (FIG. 2). The latter result indicated that use of EB had accelerated the process of affinity maturation for OVA-specific antibody. Similar to these results, mice administered a single dose of diphtheria toxin (DT) and chlamydial EB developed significantly greater serum levels of DT-specific IgG antibody (FIG. 3). In addition, these mice had reduced susceptibility to a lethal DT challenge compared to mice treated with DT alone (FIG. 4).

Disclosed herein is a vaccine comprising an antigen and a protein, peptide, or carbohydrate of *Chlamydia* spp., or a fragment thereof, wherein the antigen is not derived from a *Chlamydia* spp. The vaccine disclosed herein, which comprises both an antigen and a *Chlamydia* spp. (or a protein, peptide, carbohydrate, or fragment thereof) can increase specific humoral activity. This means that specific humoral activity can be increased by 10, 20, 30, 40, 50, 60, 70, 80, 90, or 100%, or 2, 3, 4, 5, 6, 7, 8, 9, or 10 fold or more, when compared to a control in which the antigen is administered to the subject in the form of a vaccine without a protein, peptide, carbohydrate, or fragment of *Chlamydia* spp.

The antigen and a protein, peptide, or carbohydrate of *Chlamydia* spp., or whole inactivated *Chlamydia* or a fragment thereof, can be chemically conjugated to the antigen for use as an adjuvant. Alternatively, the antigen and a protein, peptide, or carbohydrate of *Chlamydia* spp., or whole inactivated *Chlamydia* or a fragment thereof, can simply be combined without conjugation. Nanoparticles can also be used, wherein the nanoparticle is coated with a protein, peptide, or carbohydrate of *Chlamydia* spp., or whole inactivated *Chlamydia*. The protein, peptide, or carbohydrate of *Chlamydia* spp., or whole inactivated *Chlamydia* spp., can be conjugated to antigen or just combined with antigen (not chemically bound) prior to administration via the nanoparticle.

By stating that the "antigen is not derived from a *Chlamydia* spp." is meant that the antigen is not a protein, peptide, carbohydrate, nucleic acid, or fragment of any of these, which was obtained from *Chlamydia* spp. In other words, the antigen is derived from a source other than *Chlamydia*, such as another infectious agent, or from a tumor. For example, the antigen can share less than 90, 80, 70, 60, 50, 40, 30, 20, or 10% homology with a protein or nucleic acid of *Chlamydia*.

The protein, peptide, or carbohydrate of *Chlamydia* spp. (or fragment thereof) can be any functional fragment which is capable of eliciting the desired immune response. The *Chlamydia* spp. (including *C. trachomatis*, *C. psittaci* and *C. muridarum*) used in the vaccine and methods disclosed herein can be live, inactivated, or can be a protein, carbohydrate, or a fragment from *Chlamydia* spp. (including *C. trachomatis*, *C. psittaci* and *C. muridarum*). The *Chlamydia* spp. can be a variant of the known species, and still retain the function of imparting the effect disclosed herein. For example, the entire bacteria can be used (live bacteria do not infect leukocytes and cannot survive in an antibiotic-containing culture medium). Alternatively, inactivated whole bacteria (X-ray or gamma-irradiated) or lysate generated from the whole bacteria can be used. In another embodiment, specific proteins, carbohydrates, or fragments thereof can be used. For example, *Chlamydia trachomatis* major outer membrane protein (MOMP) or a fragment thereof can be used. In another example, inactivated *C. trachomatis* elementary bodies (EB) or reticulate bodies (RB) can be used. One of skill in the art can readily determine which protein, peptide, or carbohydrate of *Chlamydia* spp., or fragment thereof, can be used to impart the desired effect.

Any antigen from any disease, disorder, or condition may be used. Exemplary antigens include but are not limited to bacterial, viral, parasitic, allergens, autoantigens and tumor-associated antigens. If a DNA based vaccine is used, the antigen will typically be encoded by a sequence of the administered DNA construct. Alternatively, if the antigen is administered as a conjugate, the antigen will typically be a protein comprised in the administered conjugate. Particularly, the antigen can include protein antigens, peptides, whole inactivated organisms, and the like.

A single antigen can be used with the vaccines and methods disclosed herein, or multiple antigens can be used together. Examples include 2, 3, 4, or more antigens used in the same vaccine, or administered concurrently, or within a certain time frame of each other.

In one aspect, the antigen is selected from or derived from the group consisting of rotavirus, foot and mouth disease virus, influenza A virus, influenza B virus, influenza C virus, H1N1, H2N2, H3N2, H5N1, H7N7, HIN2, H9N2, H7N2, H7N3, H1 0N7, human parainfluenza type 2, herpes simplex virus, Epstein Barr virus, tularemia, Variola major (smallpox), viral hemorrhagic fevers, *Yersinia pestis* (plague), varicella virus, porcine herpesvirus 1, *Listeria*, cytomegalovirus, Lyssavirus, Poliovirus, Hepatitis A, Hepatitis B, Hepatitis C, Hepatitis D, Hepatitis E, distemper virus, Venezuelan equine encephalomyelitis, feline leukemia virus, reovirus, respiratory syncytial virus, Lassa fever virus, polyoma tumor virus, canine parvovirus, papilloma virus, tick borne encephalitis virus, Rinderpest virus, human rhinovirus species, Enterovirus species, Mengo virus, paramyxovirus, avian infectious bronchitis virus, human T-cell leukemia-lymphoma virus 1 human immunodeficiency virus-1, human immunodeficiency virus-2, lymphocytic choriomeningitis virus, paro-virus B 19, adenovirus, rubella virus, yellow fever virus, dengue virus, bovine respiratory syncytial virus, Corona virus, *Bordetella pertussis, Bordetella bronchiseptica, Bordetella parapertussis, Brucella ahortis, Brucella melitensis, Brucella suis, Brucella avis. Brucella* species, *Escherichia coil, Salmonella* species, *Salmonella typhi, Streptococci, Vibrio cholera, Vibrio parahaemolyticus, Shigella, Pseudomonas, Mycobacterium tuberculosis, Mycobacterium avium, Mycobacterium bovis* (Bacille Calmette Guerin), *Mycobacterium leprae, Pneumococci, Staphylococci, Enterobacter* species, *Rochalimaia henselae, Pasterurella haemolytica, Pasterurella multocida, Treponema pallidum, Haemophilus* species, *Mycoplasma bovigenitalium, Mycoplasma pulmonis, Mycoplasma* species, *Borrelia burgdorferi, Legionalla pneumophila, Colstridium botulinum, Corynebacterium diphtheriae, Yersinia entercolitica, Rickettsia ricketisii, Rickettsia typhi, Rickettsia prowsaekii, Ehrlichia chaffeensis, Anaplasma phagocytophilum, Plasmodium falciparum, Plasmodium vivax, Plasmodium malariae, Schistosomes, Trypanosomes, Leishmania* species, Filarial nematodes, Trichomoniasis, Sarcosporidiasis, *Taenia saginata, Taenia solium, Leishmania, Toxoplasma gondii, Trichinella spiralis, Coccidiosis, Eimeria tenella, Cryptococcus neoformans, Candida albican, Apergillus fumigatus, Coccidioidomycosis, Neisseria gonorrhoeae*, Malaria circumsporozoite protein, Malaria merozoite protein, Trypanosome surface antigen protein, Pertussis, Alphaviruses, Adenovirus, Diphtheria toxoid, Tetanus toxoid, meningococcal outer membrane protein, Streptococcal M protein, Influenza hemagglutinin, cancer antigen, tumor antigens, toxins, exotoxins, Neurotoxins, cytokines, cytokine receptors, nionokines, monokine receptors, plant pollens, animal dander, and dust mites. Other antigens include antigens associated with autoimmune conditions, inflammatory conditions, allergy, asthma, and transplant rejection.

Specifically, disclosed herein is a vaccine strategy for administering HIV-1 envelope glycoproteins (Env) and *Chlamydia*, which promotes both accelerated affinity maturation of HIV-specific antibody and development of antibodies with HIV-specific neutralizing activity.

Much effort has been put towards that development of Env that have the immunogenic characteristics necessary to elicit effective antibody responses with broad HIV-1 neutralizing activity. However, due to conformational and glycan shielding of conserved Ab determinants on the virus spike, HIV-1 is a highly neutralization-resistant virus. Eliciting broadly neutralizing antibodies that bind poorly to more accessible epitope regions on Env is therefore extremely challenging and requires selective targeting of specific sub-determinants and the use of potent adjuvants that increase and/or accelerate affinity maturation. As indicated above, *Chlamydia* has substantial capacity to work as an adjuvant that increases affinity maturation.

The development of a vaccine against human immunodeficiency virus (HIV) remains an unachieved goal more than three decades after its discovery. Vaccine development has been elusive and made difficult due to the fact that the virus rapidly mutates and "hides" conserved epitopes of its envelope glycoprotein by using variable loops, heavy glycosylation, oligomerization and conformational masking.

Enveloped viruses, such as HIV, enter cells by a two-step process. The first step involves the binding of a viral surface protein to receptors on the plasma membrane of a host cell. After receptor binding, a membrane fusion reaction takes place between the lipid bilayer of the viral envelope and host cell membranes. Viral proteins embedded in the lipid bilayer of the viral envelope catalyze receptor binding and membrane fusion reactions.

In HIV, the envelope (Env) glycoprotein performs the functions of viral entry. Env is synthesized as a polyprotein precursor molecule which is proteolytically processed by a host protease to generate the surface (gp120) and transmembrane subunits (gp41) of the mature Env glycoprotein complex. The unprocessed Env precursor is known as gp160, reflecting its apparent molecular mass, which is further processed to form the gp41 subunit and the gp120 subunit.

The initial step in HIV infection involves the binding of gp120 to the cell surface molecule CD4, which serves as the major receptor for HIV-I and HIV-2. The membrane fusion process is initiated by the interaction of gp120 with a G protein-coupled co-receptor, either the CCR5 or the CXCR4 chemokine receptor, generally after prior contact of gp120 with CD4. Gp41 is involved in the fusion process. The exact role of gp41 in membrane fusion is not fully understood. In one theory, gp41 first engages contact with the target cell membrane by its amino-terminal hydrophobic domain, termed the fusion peptide, and then undergoes conformation changes in order to bring the viral and cellular lipid bilayers in proximity, allowing their external leaflets to merge, thereby forming a hemifusion intermediate. Next, an aqueous connection, termed a fusion pore, must open across the internal leaflets of the merged membranes and expand to leave open passage to the nucleocapsid.

An important goal in the quest for identifying an effective HIV vaccine has been the search for a vaccine immunogen that is capable of eliciting broadly cross-reactive HIV neutralizing antibodies (bcrn Abs) (equivalently as broadly neutralizing antibodies (bn Abs)). Such antibodies are rarely elicited in HIV-infected humans, and only several such monoclonal bcrn Abs are known, which include IgG b12 (Burton et al, 1994; Roben et al., 1994), IgG 2G12 (Trkola et al., 1996; Sanders et al., 2002; Scanlan et al., 2002), ml 4 (Zhang et al., 2004c), ml 8 (Zhang et al., 2003), 447-52D (Gorny et al., 1992), IgG 2F5 (Muster et al., 1993), IgG 4E10 (Stiegler et al., 2001; Zwick et al., 2001), IgG m46 (Choudhry et al., 2007), IgG m48 (Zhang et al., 2006), Fab X5 (Moulard et al., 2002) and Fab Z13 (Zwick et al., 2001), each of which are incorporated herein by reference in their entireties.

However, even though bcrn Abs have been identified, induction of these antibodies in patients at risk of HIV infection using a vaccine have not been accomplished, as these Abs require significant somatic hypermutation and affinity maturation. Currently available adjuvants have not been able to produce these effects to the required levels. This remains one of the major hurdles in the development of a prophylactic HIV vaccines. Disclosed herein is a vaccine strategy for administering HIV-1 envelope glycoproteins (Env) and *Chlamydia*, which promotes both accelerated affinity maturation of HIV-specific antibody and development of antibodies with HIV-specific neutralizing activity, and can possibly overcome one of the major hurdles in the development of a prophylactic HIV vaccine.

In one embodiment, the antigen can comprise a tumor-related antigen. Examples of tumors that can be treated include the following: pancreatic tumors, such as pancreatic ductal adenocarinomas; lung tumors, such as small and large cell adenocarcinomas, squamous cell carcinoma, and bronchoalveolar carcinoma; colon tumors, such as epithelial adenocarcinoma and their metastases; and liver tumors, such as hepatoma and cholangiocarcinoma. Also included are breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional squamous cell carcinoma; tumors of the RES system, such as nodular or diffuse B or T cell lymphoma, plasmacytoma, and acute or chronic leukemia; skin tumors, such as malignant melanoma; and soft tissue tumors, such as soft tissue sarcoma and leiomyosarcoma. Of especial interest are brain tumors, such as astrocytoma, oligodendroglioma, ependymoma, medulloblastomas, and primitive neural ectodermal tumor. Included in this category are gliomas, glioblastomas, and gliosarcomas.

Specifically, the following antigens are associated with the following types of cancer, and can be used in the vaccines and methods disclosed herein:

TABLE 1

| Cancers and Associated Antigens | |
| --- | --- |
| Melanoma | Tyrosinase, Tyrosinase-related protein (Trp-1), gp 100, Melan/MART-1 |
| Prostate adenocarcinoma | Prostate-specific membrane antigen, Prostate-specific acid phosphatase, Prostate specific antigen |
| Pancreatic, lung, breast and colon adenocarcinoma | MUC1 |
| Non-small-cell lung carcinoma | MUC1, MAGE antigens, EGFR |
| Cancer/testis antigens | LAGE/NY-ESO1, MAGE antigens, CEA, AFP |
| Breast cancer | HER-2 |
| Acute myelogenous leukemia | Aurora-A kinase, BRAP, Cyclin A1, hTert, WT1 |
| Chronic lymphocytic leukemia | ROR1 |
| Chronic myelogenous leukemia | BCR/ABL, BRAP, CML28, CML66, PR1, Proteinase 3, survivin, WT1 |

The immune status of the individual may be any of the following: The individual may be immunologically naïve with respect to certain tumor-associated antigens present in the composition, in which case the compositions may be given to initiate or promote the maturation of an anti-tumor response. The individual may not currently be expressing anti-tumor immunity, but may have immunological memory, particularly T cell memory relating to a tumor-associated antigen comprised in the vaccine, in which case the compositions may be given to stimulate a memory response. The individual may also have active immunity (either humoral or cellular immunity, or both) to a tumor-associated antigen comprised in the vaccine, in which case the compositions may be given to maintain, boost, or maturate the response, or recruit other arms of the immune system. The subject should be at least partly immunocompetent, so that the vaccine can induce endogenous T cell responses.

Disclosed herein is a kit comprising an antigen and a protein, peptide, or carbohydrate of Chlamydia spp., or a fragment thereof, wherein the antigen is not derived from a Chlamydia spp. The kit can comprise other components needed for a vaccine as well, as disclosed herein.

Also disclosed herein are methods of treating or preventing a disease. These methods comprise administering to a subject an antigen, wherein the antigen is not derived from Chlamydia spp.; and a protein, peptide, or carbohydrate of Chlamydia spp., or a fragment thereof, thereby preventing a disease or infection in the subject. The antigen and the protein, peptide, or carbohydrate of Chlamydia spp., or a fragment thereof, can be given simultaneously, such as in the same injection. Alternatively, the antigen and the protein, peptide, or carbohydrate of Chlamydia spp., or a fragment thereof, can be given separately. One of skill in the art will appreciate the various methods that can be used to administer the vaccine.

The subject being treated can have a variety of diseases or disorders. Any disease or disorder which can be treated using the humoral arm of the immune system can be treated using the methods disclosed herein. For example, infectious diseases and cancer can be treated using these methods.

Disclosed herein is a strategy for immunization to elicit an immune response directed against an antigen. The vaccine can be used to treat or prevent HIV, for example. In one embodiment, disclosed is a subject with a type of cancer which expresses a tumor-specific antigen. This can result in an improved therapeutic outcome for the patient, evidenced by, e.g., a slowing or diminution of the growth of cancer cells or a solid tumor which expresses the tumor-specific antigen, or a reduction in the total number of cancer cells or total tumor burden. In a related embodiment, the patient has been diagnosed as having a viral, bacterial, fungal or other type of infection, which is associated with the expression of a particular antigen, e.g., a viral antigen. This vaccine can result in an improved therapeutic outcome for the patient as evidenced by a slowing in the growth of the causative infectious agent within the patient and/or a decrease in, or elimination of, detectable symptoms typically associated with the particular infectious disease.

When the vaccine is prepared for administration, it can be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" substance is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

The expression vectors, transduced cells, polynucleotides and polypeptides (active ingredients) can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Pharmaceutical formulations containing the therapeutic agents disclosed herein can be prepared by procedures known in the art using well known and readily available ingredients. The therapeutic agents can also be formulated as solutions appropriate for parenteral administration, for instance by intramuscular, subcutaneous or intravenous routes. The pharmaceutical formulations of the therapeutic agents can also take the form of an aqueous or anhydrous solution or dispersion, or alternatively the form of an emulsion or suspension.

The dose given is an amount "effective" in bringing about a desired therapeutic response, be it the stimulation of an immune response, or the treatment of infectious disease or cancer as defined elsewhere in this disclosure. Multiple doses when used in combination to achieve a desired effect each fall within the definition of an effective amount. The doses can be given multiple times a day, or every day, or every other day, or every third day, etc. Additional doses may be given, such as on a monthly or weekly basis, until the desired effect is achieved. Thereafter, and particularly when the immunological or clinical benefit appears to subside, additional booster or maintenance doses may be given as required.

The various components of the vaccine are present in an "effective combination", which means that there are sufficient amounts of each of the components for the vaccine to be effective. Any number of constituents may be used, as long as the vaccine is effective as a whole. This will also depend on the method used to prepare the vaccine.

The pharmaceutical compositions may be given following, preceding, in lieu of, or in combination with, other therapies relating to generating an immune response or treating or preventing an infection. For example, the subject can be given an antiviral medication as well. Where such modalities are used, they are preferably employed in a way or at a time that does not interfere with the immunogenicity of the compositions disclosed herein. The subject may also have been administered another vaccine or other composition in order to stimulate an immune response.

Disclosed herein are combination therapies, comprising administration of a vaccine combination described herein in conjunction with another strategy aimed at providing an anti-tumor or anti-pathogen immunological response. In one combination therapy, the subject is given the vaccine disclosed herein, along with an antiviral therapy known to those in the art. In one combination therapy, the subject is given an intra-tumor implant of stimulated allogeneic lymphocytes, either before, during, or after treatment at a site distant from the tumor. In another combination therapy, the subject is treated at sites distant from the tumor with an alternative vaccine composition, either before, during, or after treatment. Where a plurality of different compositions or modes of administration are employed throughout the course of therapy, the order and timing of each element of treatment is chosen to optimize the immunostimulatory or anti-tumor effect.

A number of embodiments of the invention have been described. Nevertheless, it will be understood that various modifications may be made without departing from the spirit and scope of the invention. Accordingly, other embodiments are within the scope of the following claims.

EXAMPLES

Figure 1:
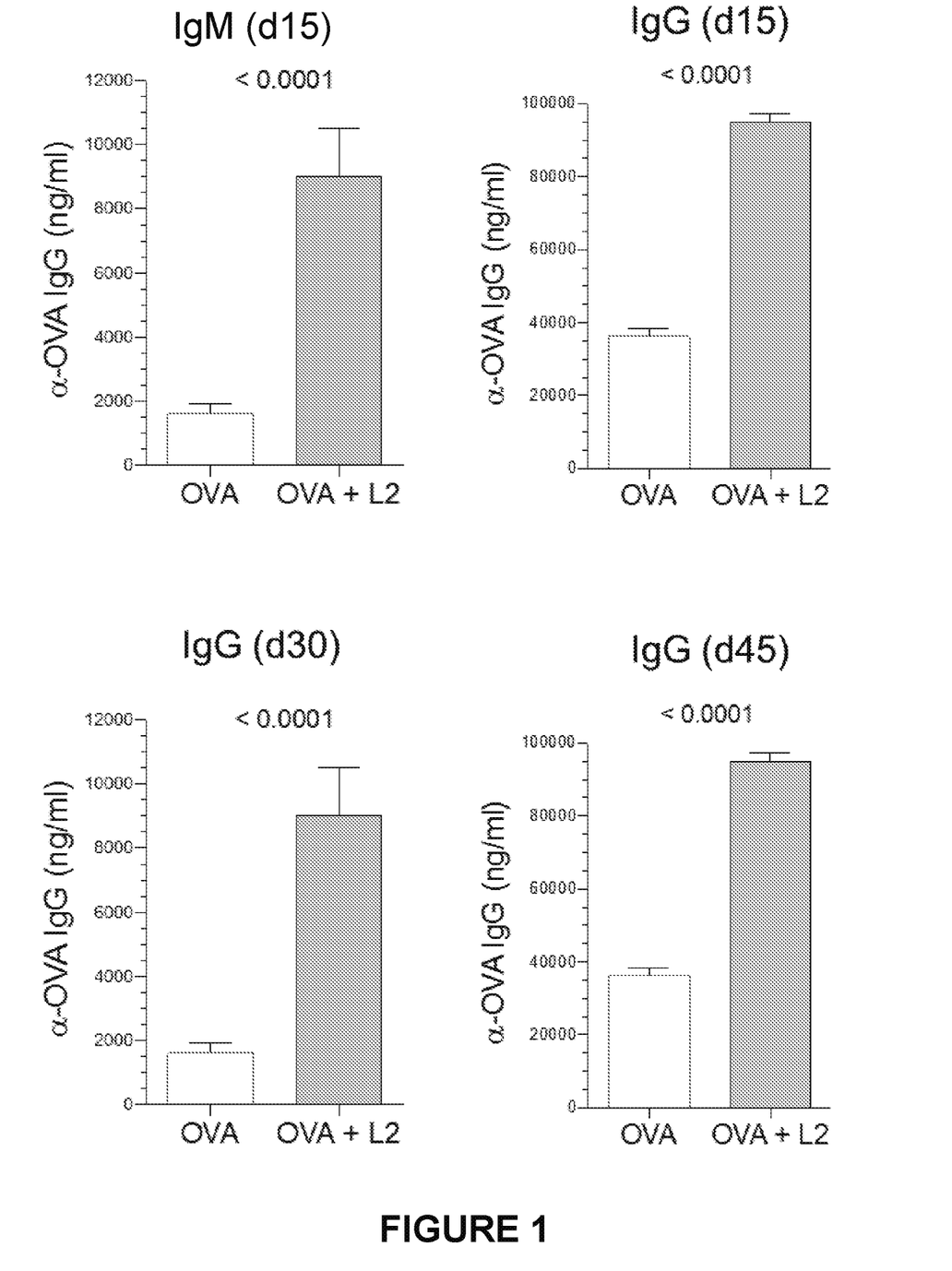
Figure 2:
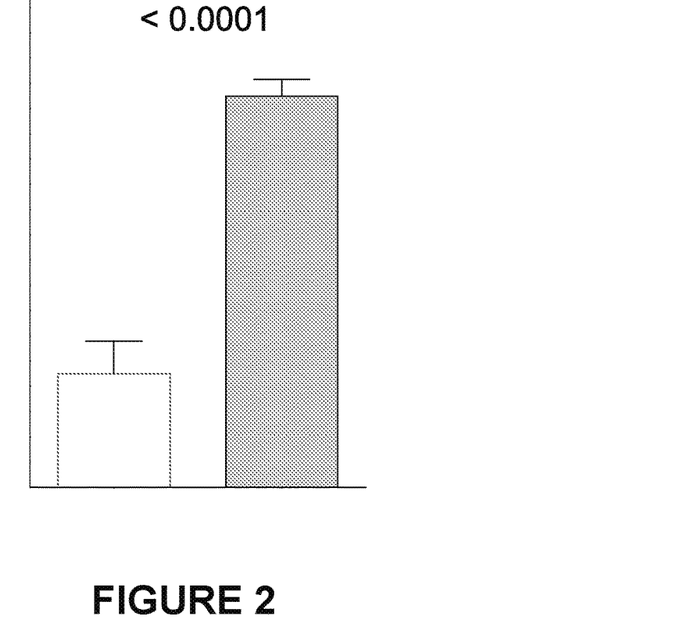
Figure 3:
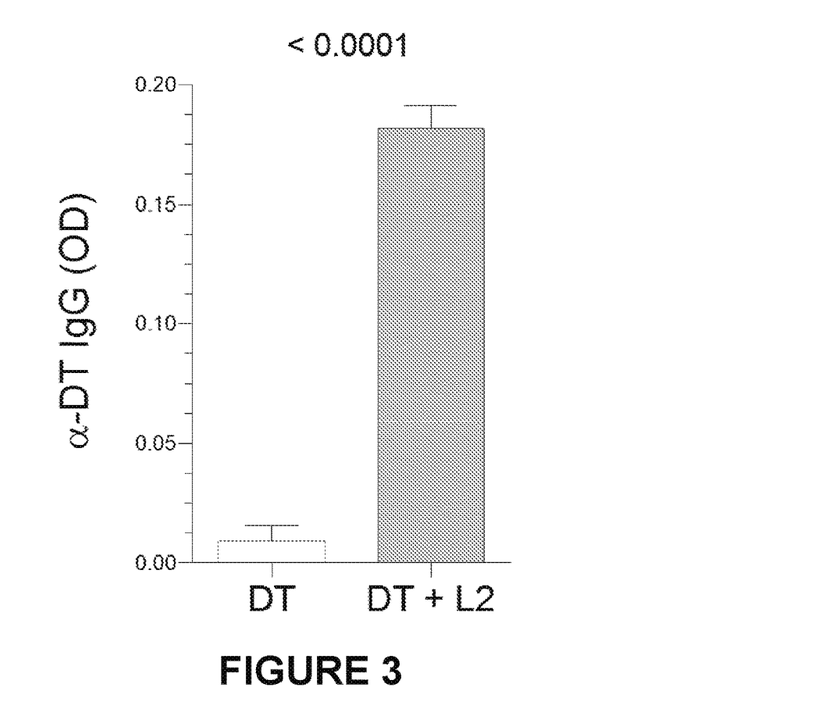
Figure 4:
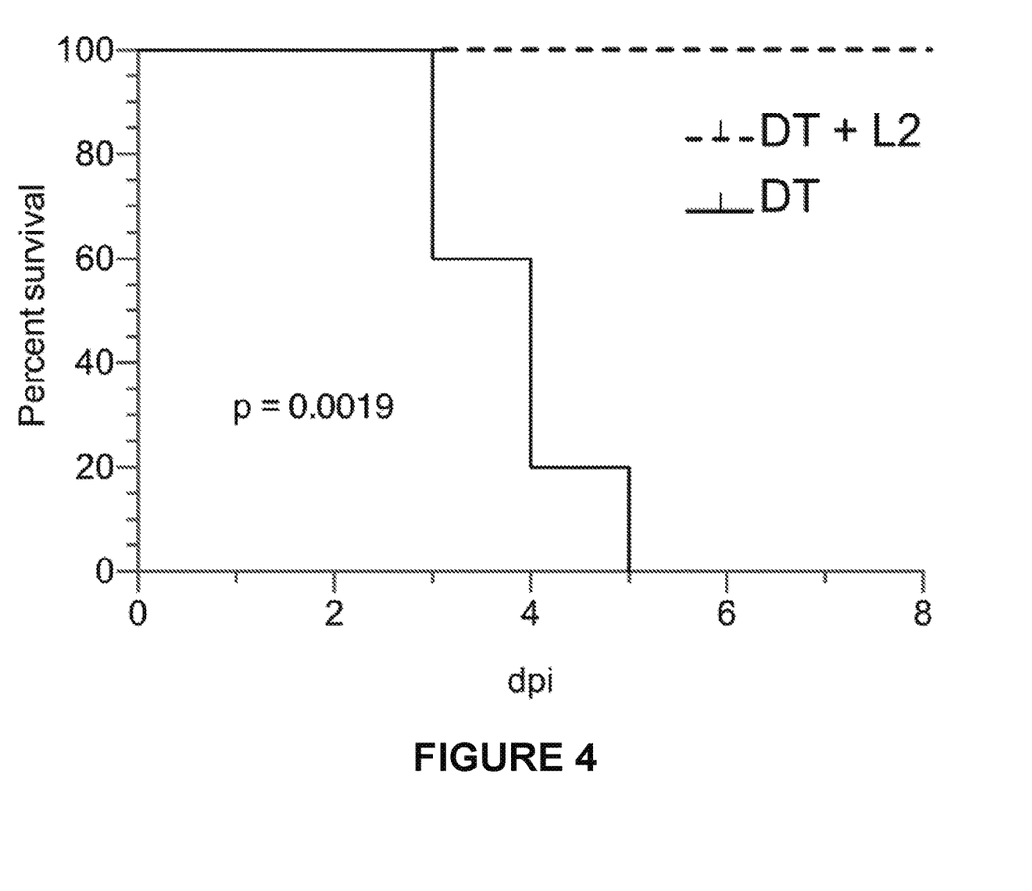

Example 1: *C. trachomatis* Accelerates Affinity Maturation of OVA-Specific Antibody Mice ovalbumin (OVA) and inactivated *C. trachomatis* elementary body (EB) were administered every 2 weeks for a month (i.e., a total of 3 treatments). In this study, these mice displayed significantly higher OVA-specific IgM and IgG serum antibody levels compared to mice receiving OVA alone (FIG. 1), and OVA-specific antibody affinity was significantly higher in mice concomitantly treated with OVA and chlamydial EB (FIG. 2). The latter result indicated that use of EB had accelerated the process of affinity maturation of the OVA-specific antibody. Similar to these results, mice administered a single dose of diphtheria toxin (DT) and chlamydial EB developed significantly greater serum levels of DT-specific IgG antibody (FIG. 3). In addition, these mice had reduced susceptibility to a lethal DT challenge compared to mice treated with DT alone (FIG. 4).

Example 2: *C. trachomatis* can Increase Env-Specific Antibody Responses

In vivo studies using mice as an initial experimental platform can be performed. It is determined whether *Chlamydia* can increase the immunogenicity of Env in C57BL/6 mice by determining the magnitude of antigen-specific responses by ELISA and B cell ELISPOT measurements. The avidity of the Env-specific antibody responses is then defined by using the chaotropic ELISA protocols. Subsequently, single Env-specific memory B cells and germinal center B cells are identified and isolated from immunized C57BL/6 mice to determine if *Chlamydia* was able to increase the degree of somatic hypermutation. *Chlamydia* is also assessed as an adjuvant to increase the capacity of the elicited Env-specific antibodies to neutralize HIV-1 using a well-standardized Env pseudovirus assay and TZM-b1 target cells. Finally, the ability of *Chlamydia* to act as a B cell adjuvant to increase the levels and affinity of Env-specific antibodies when used concomitantly with other types of adjuvants such as mineral salts (e.g. Alum), oil emulsions (e.g. MF59), and particulates (e.g. AbISCO-100) can be assessed.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An immunogenic parenteral solution comprising an antigen and an effective amount of an adjuvant, wherein the adjuvant comprises a separate, whole, inactivated *Chlamydia* spp. bacteria, wherein the antigen is not derived from a *Chlamydia* spp., and further wherein the antigen comprises a tumor antigen.

2. The immunogenic parenteral solution of claim 1, wherein the *Chlamydia* spp. comprises *C. trachomatis, C. psittaci, C. muridarum*, or *C. pneumoniae*.

3. The immunogenic parenteral solution of claim 1, comprising more than one antigen.

4. The immunogenic parenteral solution of claim 3, comprising more than two antigens.

5. The immunogenic parenteral solution of claim 1, wherein the parenteral solution comprises a carrier such an oil, saline, aqueous dextrose, glucose, or a related sugar solution.

6. The immunogenic parenteral solution of claim 1, wherein the parenteral solution comprises glycol.

7. The immunogenic parenteral solution of claim 6, wherein the glycol comprises propylene glycol or polyethylene glycol.

8. The immunogenic parenteral solution of claim 1, wherein the parenteral solution comprises a stabilizing agent.

9. The immunogenic parenteral solution of claim 8, wherein the stabilizing agent comprises sodium bisulfate, sodium sulfite or ascorbic acid.

10. The immunogenic parenteral solution of claim 1, wherein the parenteral solution comprises citric acid or sodium ethylenediaminetetraacetic acid (EDTA), benzalkonium chloride, methyl- or propyl-paraben or chlorobutanol.

11. The immunogenic parenteral solution of claim 1, wherein the parenteral solution comprises a control release preparation.

12. The immunogenic parenteral solution of claim 11, wherein the control release preparation comprises polymers, polyesters, polyamino acids, polyvinyl, pyrolidone, ethylenevinylacetate, methyl cellulose, carboxymethyl cellulose or protamine sulfate.

13. The immunogenic parenteral solution of claim 1, wherein the parenteral solution is incorporated into particles of polymeric materials.

14. The immunogenic parenteral solution of claim 13, wherein the polymeric material comprises polyesters, polyamino acids, hydrogels, poly (lactic acid) or ethylenevinylacetate copolymers.

15. The immunogenic parenteral solution of claim 1, wherein the antigen and the separate, whole, inactivated *Chlamydia* spp. are chemically conjugated.

16. The immunogenic parenteral solution of claim 1, wherein the antigen and the separate, whole, inactivated *Chlamydia* spp. are in or on a nanoparticle.

* * * * *